(12) United States Patent
Barth et al.

(10) Patent No.: US 8,331,634 B2
(45) Date of Patent: Dec. 11, 2012

(54) METHOD FOR VIRTUAL ADAPTATION OF AN IMPLANT TO A BODY PART OF A PATIENT

(75) Inventors: Karl Barth, Höchstadt (DE); Gerd Wessels, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 1072 days.

(21) Appl. No.: 11/861,407

(22) Filed: Sep. 26, 2007

(65) Prior Publication Data
US 2008/0077003 A1  Mar. 27, 2008

(30) Foreign Application Priority Data
Sep. 26, 2006 (DE) .......................... 10 2006 045 400

(51) Int. Cl.
*G06K 9/00* (2006.01)
*A61F 2/32* (2006.01)
(52) U.S. Cl. .................................... 382/128; 623/22.11
(58) Field of Classification Search .................. 382/128; 600/407; 623/22.11
See application file for complete search history.

(56) References Cited

U.S. PATENT DOCUMENTS

| | | | |
|---|---|---|---|
| 4,695,283 A | 9/1987 | Aldinger | |
| 4,704,686 A | 11/1987 | Aldinger | |
| 4,995,883 A * | 2/1991 | Demane et al. | 623/22.42 |
| 5,007,936 A * | 4/1991 | Woolson | 128/898 |
| 5,769,092 A | 6/1998 | Williamson, Jr. | |
| 5,798,924 A | 8/1998 | Eufinger et al. | |
| 5,824,085 A * | 10/1998 | Sahay et al. | 128/898 |
| 6,205,411 B1 * | 3/2001 | DiGioia et al. | 703/11 |
| 6,301,495 B1 * | 10/2001 | Gueziec et al. | 600/407 |
| 6,424,332 B1 * | 7/2002 | Powell | 345/156 |
| 2005/0027187 A1 | 2/2005 | Barth et al. | |
| 2005/0203384 A1 * | 9/2005 | Sati et al. | 600/426 |
| 2005/0256389 A1 | 11/2005 | Koga et al. | |
| 2008/0269596 A1 * | 10/2008 | Revie et al. | 600/424 |

FOREIGN PATENT DOCUMENTS

| EP | 1 406 203 A2 | 4/2004 |
|---|---|---|
| EP | 1 598 778 A1 | 11/2005 |
| WO | WO 98/14128 | 4/1998 |

OTHER PUBLICATIONS

"An Image-Directed Robotic System for Precise Orthopaedic Surgery," Russell H. Taylor, et al, IEEE Transactions on Robotics and Automation. vol. 10, No. 3, Jun. 1994, pp. 261-275.*
"OrthoDock an Image Driven Orthopaedic Surgical Planning System," William A. Hanson, et al, Annual International Conference of the IEEE Engineering in Medicine and Biology Society, vol. 12, No. 5, 1990, pp. 1931-1932.*
"An Image-Guided Planning System for Endosseous Oral Implants," Verstreken et al., IEEE Trans. on Medical Imaging, vol. 17, No. 5 (Oct. 1998), pp. 842-852.

* cited by examiner

*Primary Examiner* — Wenpeng Chen
(74) *Attorney, Agent, or Firm* — Schiff Hardin LLP

(57) ABSTRACT

In a method for virtual adaptation of an object to be medically inserted in a patient, to a body part of the patient, the object is shown in a desired view on a monitor, the body part is shown in 3D on the monitor, the body part in its unchanged 3D-imaging context, is automatically displaced relative to the object until the object is adapted to the body part with the orientation of the object relative to the monitor remaining unchanged.

9 Claims, 8 Drawing Sheets

METHOD FOR VIRTUAL ADAPTATION OF AN IMPLANT TO A BODY PART OF A PATIENT

BACKGROUND OF THE INVENTION

1. Field of the Invention

The present invention concerns a method for virtual adaptation of an implant to a body part of a patient.

2. Description of the Prior Art

Today prostheses or implants that are inserted into patients are often used in surgery, in particular in orthopedic surgery. Strictly speaking, prostheses are normally replications or replacements for body parts of a patient; implants are mainly abstract components such as, for example, plates or screws. For simplification, however the term "implant" will be used herein to encompass both implants in the actual sense as well as prostheses.

It is important to insert the implants into the patients with optimally exact fit and to optimally plan their insertion and to select a suitable implant for the insertion. Techniques derived, for example, from computer aided design (CAD) are increasingly required and utilized in the medical field for this purpose.

In the predominant number of cases, conventional (also film-based) x-ray exposures and hardcopy blueprints of implants represent the basis of a surgical planning. Construction or adaptation is done manually, virtually with pencil and tape measure, in order to find an optimal correct fit. Systems in which the x-ray image and/or the scale drawing of the implant already exist digitally represent an advance, but this case is predominantly limited to two-dimensional representations.

The geometries of the implants nearly exclusively exist only in 2D coordinates. Medical imaging, for example on the basis of computer tomography or the 3D C-arm technique, increasingly ensues in 3D. There are therefore newer approaches that describe concepts that also support the planning in three dimensions. These known techniques, however, are not very suitable for use in a procedure and that is only two-dimensional, and they do not proceed automatically, least of all for repositioning (i.e. the reconstruction of, for example, a fragmented bone after a fracture).

An example is U.S. Pat. No. 5,769,092, which discloses how bone cement can be removed in a computer-aided manner in order to replace an old prosthesis with a new one. Only standard representations parallel or orthogonal to the DICOM coordinate system are described therein, and the method is purely interactive, meaning that no automatic adaptation (for example of an implant in a bone) ensues based on pattern recognition.

Similar considerations apply to DE 43 41 367 C1, wherein interactive adaptation is likewise described. The article by K. Verstreken et al., "An Image-Guided Planning System for Endosseous Oral Implants", IEEE Tran. Med. Im. Vol. 17, No. 5, October 1998 concerns improvements in 2D planning using 3D information. The primary emphasis therein is the use of automatic 3D contour and surface determination (segmentation), which ultimately is used again only in the basically 2D-oriented, interactive planning followed by 3D visualization and monitoring.

EP 0 093 869 A1 describes relatively briefly how individual prostheses and implants can be produced with an exclusively layer-based, slice-oriented method. For this purpose, it is proposed (without describing the technical realization in detail) to connect the layers (slices). From a modern point of view this is trivial and is limited to a procedure parallel to the table feed of the computed tomography apparatus. It is not described how 3D object adaptation can be implemented in free orientation with high resolution, and there is no consideration of how the adaptation can be implemented automatically, or how the adaptation can be supported by simultaneous complementary displays freely oriented in space.

WO 98/14128 likewise describes a method in the field of computer-aided prosthesis planning. This again is a predominantly two-dimensional approach: although (3D) CT input data exist, the adaptation ensues in two-dimensional slices (cross-sections). Nothing is said about how a positioning in isotropic space can be automated.

SUMMARY OF THE INVENTION

An object of the present invention is to provide a method that allows an optimal adaptation of implants in more than two dimensions.

The object is achieved by a method according to the invention that is a virtual method (thus not a method acting on the patient) which, for example, is implemented at a computer system. The method serves only for planning of the adaptation of the object and thus not for actual implementation of the medical treatment on the patient.

The inventive method is based on the use of a procedure reversed from the customary workflow of the execution.

The object is achieved in accordance with the present invention by a method for virtual adaptation of an object to be inserted in a patient, to a body part of the patient, wherein the object is shown in a desired view on a monitor, the body part is also shown on the monitor in 3D, and the body part, in an unchanged imaging context, is automatically displaced relative to the object until the object is adapted to the body part, with the position and orientation of the object relative to the monitor remaining unchanged.

The object to be adapted thus is initially presented in a desired view on a monitor (screen). The object can be an implant in the above sense (thus also a prosthesis) or, for example, a fragment of a body part, bone or the like that is to be repositioned on the body part.

The presentation on the screen (which, for example, belongs to a CAD computer workstation) normally includes one or more screen windows with one or more differing views, i.e. viewing directions to the object. The desired view means that, for the observer of the screen, the object is presented in the view that is preferred by the viewer and is deemed to be advantageous.

The desired (preferred) view then allows, for example, a best-possible optical monitoring of whether the object is actually optimally adapted to the body part at its end.

The body part is subsequently presented in 3D together with the object on the screen, likewise in corresponding views, and is automatically displaced relative to the object until the desired adaptation of the object to the body part is achieved. In other words, the body part is moved and rotated around the virtual object (which object is anchored in a stationary manner), or is displaced relative to this object. Since the object is shown in a desired view from the beginning, the correct adaptation of the object can be clearly documented or, respectively, checked after an occurred adaptation.

The body part is shown together with the remaining 3D data of the patient (i.e. permanently embedded in the remaining volume data), thus moved in an unchanged image context.

Since the object is shown in a desired manner, the method allows an improved, more precise monitoring at arbitrary points of the object and primarily also in the further environment of the object after an occurred automatic adjustment of the presentation on the screen.

The presentation in more than two dimensions on a screen is dependent on the possibilities of the source image data, thus the image data for object and body part or, respectively, the CAD-like description data of the object. In other words, the planning in three dimensions can ensue more completely and more precisely the more 3D information about body part and object are available. The inventive method proceeds such that it is first and foremost sought to adapt the image data, or a selection of the image data, to a desired physiological form or an implant form. After completion of this adaptation (thus this matching for, for example, a rotated and displaced bone part), possible deviations for the associated other body parts are directly visible. The respective 3D image data of object and body part are not altered during the automatic adaptation, but are visualized in an improved manner. The described, finished adaptation of the representation of the body part to the desired form or implant form is described by a 4×4 transformation matrix. The transformation that would be required in the patient to set the bone is calculated by inversion of this 4×4 transformation.

Complete, nearly isotropic volume data sets (for example on the basis of computer tomography (CT)) are increasingly used as image material of patients and/or implants in medical technology. The inventive method is predominantly oriented on this. Such a "complete" three-dimensional data set possesses the advantages that they can be arbitrary visual navigation is possible in these data and that in every position the body structures (such as, for example, bones) are shown with full sharpness in a volume image without overlapping. The scaling is well-defined and reliable overall, constant over the entire volume and already attainable from the DICOM description of the data set. For real 3D representations it is necessary in the inventive method to implement the correct adaptation of the object by a transparent representation or by another technique of virtual immersion in the object volume. In this context MPR, volume rendering, MIP and SSD or 3D stereo representation are suitable as three-dimensional presentation formats on a screen. These methods are normally linked with a type of automatic clipping in order to ensure the precise adaptation inside the volume.

The inventive method thus serves merely for support of the surgical implant or bone-setting planning in which the adjustment of the 3D visualization and the virtual (re)positioning of body parts, implants and/or the prostheses ensue automatically. The implant is normally shown in a characteristic (for example central) section. The image data of the patient or body part are normally superimposed on or placed in the background of the image of the implant possibly with a fading (blending) technique. The adaptation ensues automatically or iteratively. An adaptation is then achieved when the body part optimally fits with or optimally overlaps the implant. A manual displacement and rotation for monitoring or manual correction can also ensue after every iterative step.

In the case of the implant as the object, in the inventive method the dimensions of the implant can be varied and the method can subsequently be implemented again as described above. An implant variant altered according to scale is thus again automatically adapted to the body part. It can thus be established which of the two different implant variants can be better adapted to the body part. By iterative size (scale) variation and adaptation, an implant version can thus be found that has an optimal size with regard to the body part, thus can overall be optimally adapted to the body part.

Given variation of the size of the implant, its dimensions can be altered to scale. The basic shape of all implant versions is retained and the shape is only scaled, for example to patients of different sizes.

The implant also can be varied to allow versions of the implant to be selected that differ in terms of their dimensions from those of an implant database. In other words, since various commercially available implants are stored in the implant database, the correct implant that can be optimally adapted to the body part of the patient can be selected from a product catalog. Furthermore, an intelligent database can be provided that enables a continuous form variation (morphing) of the implant through a parameter control. An example for this is the adjustment of one or more curvature parameters given curved or flexible implants. These implants are selected with specific virtual curvature and are adapted in the same manner. After finished, optimized adaptation, possibly with various parameter alternatives, the optimal form is clear and this can be correctly bent in a suitable machine in preparation for the actual therapy.

Some implants are modularly designed, i.e. composed of at least two components. Such an implant can be altered by respective, different components being selected from a component database of available components and being assembled into different implant versions. An automatic adaptation as described above is then implemented again for each implant version (variant) and an optimal implant version is found for the patient.

Sometimes only two-dimensional data exist for the object. For a metal plate, for example, its x-y dimensions are stored as an outline shape. In order to generate a three-dimensional model of the implant for the inventive method, 3D data can be generated from the 2D data based on known symmetries or prior knowledge. For the metal plate cited above, for example, its thickness in the z-direction is known. The 2D data can then be extrapolated into 3D image data via the prior knowledge of the thickness. Further examples of prior knowledge are, for example, rotation symmetry for implants for which only a 2D section exists, or a right-left mirror symmetry for implants or body parts or their fragments for which data exist only for one side of the body, for example.

As mentioned above, the 3D representations of object and body part can be shown on a monitor. This firstly allows the free rotation of the object for selection of the desired view.

A fit size (toleranced dimension) can be determined for the adaptation of object and body part. The fit size supplies an objective measure about the quality of the adaptation of the object to the body part, for example in the form of a numerical value that is maximal or minimal given an optimal adaptation. This fit size can in particular be used for the automatic implementation of the adaptation.

A fit size can be, for example, the value of the cross-correlation between the voxels of the implant and the voxels of the body part. This can be explained in the example of the ball head part for an artificial hip joint. For example, the central section of the artificial joint ball is initially shown with a radius enlarged by, for example, 5 mm. The approximate positioning now ensues by superimposition of the focal points of the projected, imaged structures of the artificial hip joint and the real hip joint to be replaced. In order to now locate the central section in the 3D data set of the body part, thus of the hip head to be replaced, the entire dimensional range under consideration is traversed step-by-step. For each stage a correlation of the voxel values of the artificial ball with the voxel values of the real hip head is implemented. The central section through the head to be replaced is reached for the maximum correlation value. This position is now maintained and the radius of the implant is reset to the original value and checked for optimal fit (that would be a cross-correlation factor of 1.0), or a refined size adaptation is made. The adaptation of the position in the body part and the size adaptation and selection of the implant can also alternately be implemented iteratively.

The inventive method can be implemented in the context of a medical procedure to be conducted on a patient. The workflow of the medical procedure can then be modified based on the result of the virtual adaptation of the object to the body part, meaning that workflow steps of the medical measure are correspondingly executed dependent thereon. For example, the medical measure can be promptly begun when an implant of correct dimensions is provided on site for the patient in the OR (operating room) as a result of execution of the inventive method.

In particular, inventory planning or material provision or accounting dependent on the adaptation of the implant or the results of the adaptation can be implemented in the medical workflow. The virtual adaptation of the implant thus enables a corresponding optimization of the workflow for the actual medical procedure.

DESCRIPTION OF THE PREFERRED EMBODIMENTS

The following exemplary embodiment describes the virtual preoperative placement and adaptation of an artificial hip joint 2 as an object in a patient 4 by a physician 10. The method exemplarily operates with the MPR representation of image data on a monitor 6 of a medical operation planning workstation (CAD system) (not shown).

Figure 1:
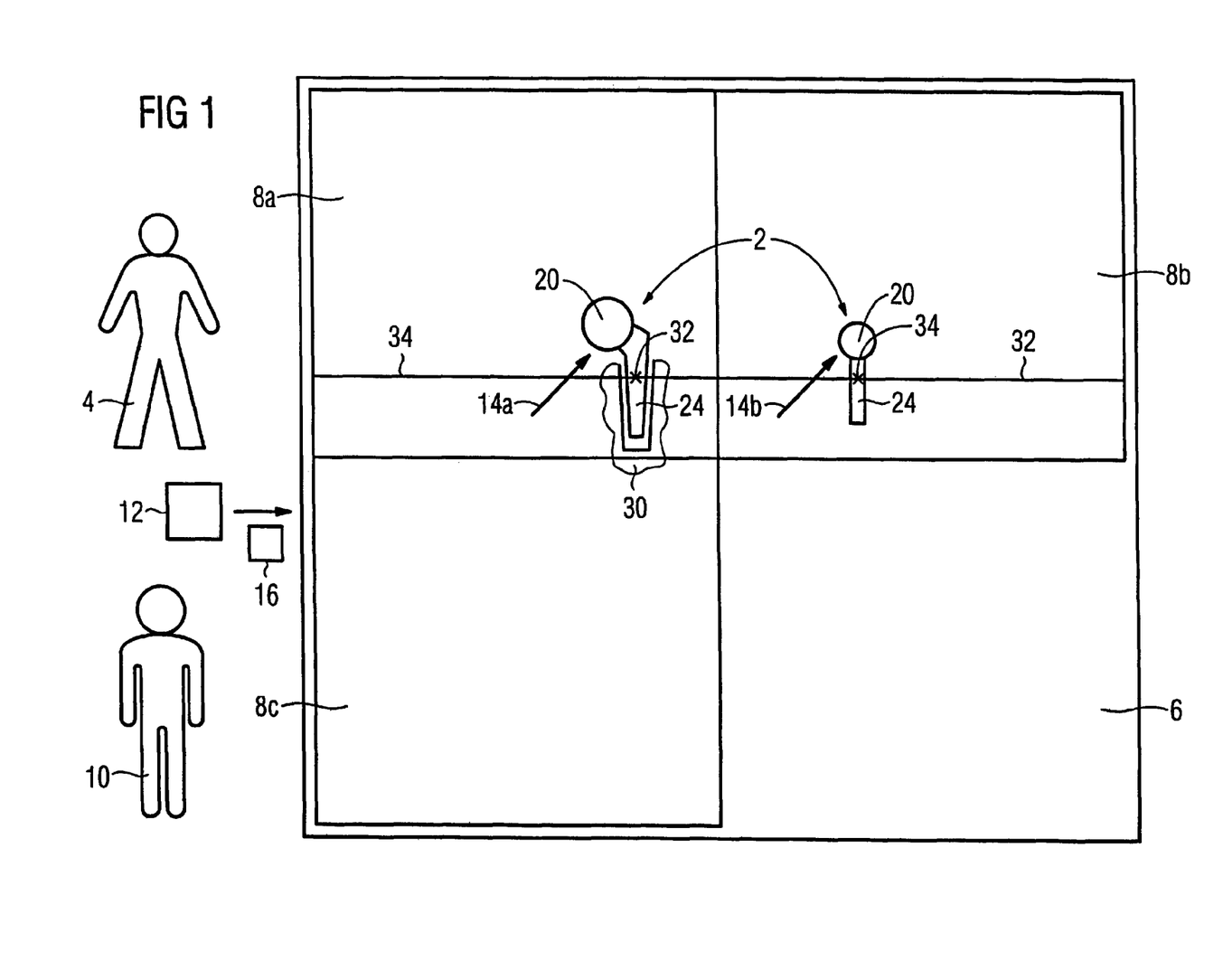
FIG. 1 schematically illustrates the monitor of an operation planning workstation for a hip prosthesis planning on a patient by a physician, with a shown possible implant.

FIG. 1 shows the monitor 6 on which three windows 8*a-c* are shown. The windows 8*a-c* correspond to the arrangements of a frontal (8*a*), lateral (8*b*) and axial (8*c*) view that are typical for medical 3D views, for example for a patient-related image data. Operator of the method is the physician 10 who, dependent on the patient 4 (for example according to the patient's body size), selects a hip joint 2 deemed, from the size, as approximately fitting from a number of available hip joints in an implant database 12. For representation of the hip joint 2 on the monitor 6, its 3D image data 16 are taken from the database 12. The selected hip joint 2 is then presented on the monitor 6, and the physician 10 places this by displacement and rotation on the monitor 6 such that the views desired by the physician are presented in the windows 8*a* and *b*, thus frontal and lateral. The desired views thereby refer to the viewing directions 14*a,b* from which the hip joint 2 is shown on the screen 6. In the example the viewing directions 14*a* and 14*b* are arranged perpendicular to one another. An axial presentation of the hip joint 2 in the window 8*c* does not occur in the example.

Alternatively, the 3D image data 16 of the hip joint 2 could be generated such that only 2D scale drawings (not shown) of the hip joint are taken from the database 12 and these are converted (transformed) in advance into 3D data as image data 16.

Figure 2:
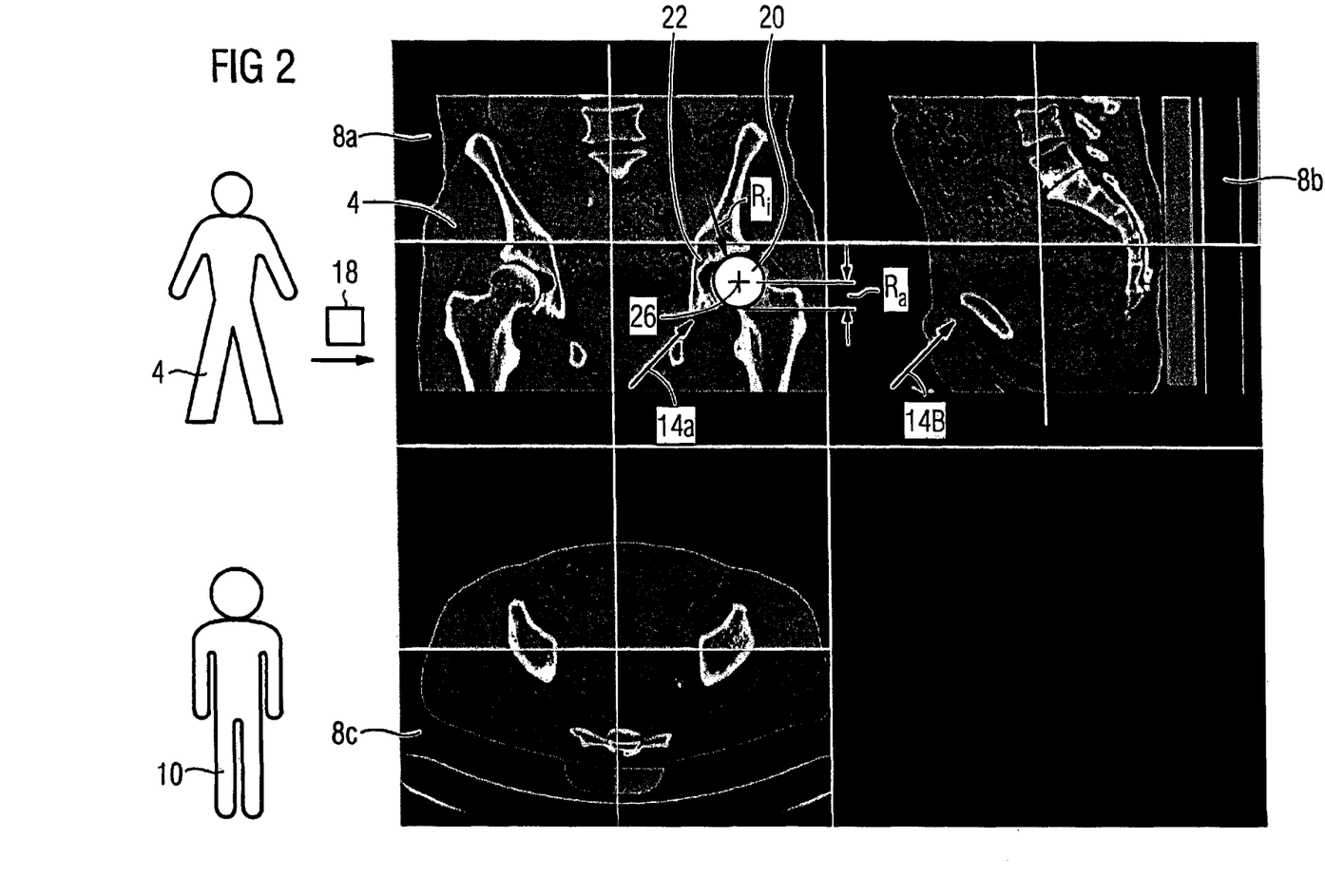
FIG. 2 shows the monitor of FIG. 1 with a part of the hip prosthesis and an x-ray image of the patient.

FIG. 2 shows how, in a next method step of the presentation of the hip joint 2, 3D image data 18 of the patient 4 are now superimposed; these 3D image data 18 are thus simultaneously shown in the windows 8*a*-8*c*. The viewing direction 14*a* toward the hip joint 2 that is established once thereby always remains unchanged in the window 8*a* as it was in FIG. 1. The image data 18 are thus aligned relative to the hip joint 2.

Here FIG. 2 merely shows the ball head 20 of the hip joint 2 that is to be placed in the acetabulum 22 of the patient 4 as a body part or is to be optimally fitted in this. The implant shaft 24 of the hip joint 2 is thus masked out. The representation of the hip joint 2 is colored and/or emphasized in brightness against the image data 18 of the patient 4. The relative orientation of patient 4 relative to ball head 30 that is shown in FIG. 2 results from typical experiential values, for example as an average position of a representative patient group (statistical base). The frontal and lateral presentation of the hip joint 2 in the windows 8*a* and 8*b* ensues in the same orientation as for an average patient of the group.

Since the ball head 20 should initially be only frontally adapted, it is masked out in the window 8*b*.

Starting from the initial position shown in FIG. 2, the position of the acetabulum 22 relative to the ball head 20 is automatically determined. The approximate position of the rotation center 26 of the joint socket 22 and its inner radius $R_i$ are known from the implant geometry (thus in the example the dimensions of the ball head 20) and from data of the aforementioned patient collective. It is left to the physician 10 to also implement a manual (correction) positioning of the ball head 20 in the acetabulum 22.

The automatic fine positioning now ensues: starting from the start position shown in FIG. 2, the optimal fit (outer radius $R_a$) and the position of the ball head 20 are sought in which the two-dimensional circular shape of the ball head 20 shown in the window 8*a* is adapted in terms of its orientation and position to the natural joint socket 22, or its inner contour. A distinctly larger circular shape, thus a ball head 20 of greater diameter $R_a \gg R_i$, is selected as a start value. The 3D image data 18 of the patient 4 are then displaced relative to the window 8*a*-8*c* (and therewith relative to the ball head 20 positioned fixed in the windows 8*a*-8*c*) until a good correlation of the circular shape (thus of the ball head 20) with the anatomy (thus the acetabulum 22) of the patient 4 is present. In other words, in window 8*a*, for example, that slice depth in the 3D image data 18 is sought that satisfies the aforementioned criteria. In the image plane of the window 8*a*, the greatest width in the anatomy of the patient 4 (thus the greatest inner radius $R_i$ of the acetabulum 22) is then measured. After the occurred displacement of the image data 18, a relative position of patient 4 and ball head 20 (and thus an altered position of the rotation center 26) which is now improved with regard to the anatomy of the patient 4 relative to the generally applicable patient collective, which relative position is altered relative to FIG. 2, normally results after the displacement of the image data 18. The outer radius $R_a$ of the ball head 20 can then be reduced step-by-step until it is optimally adapted to the size of the acetabulum 22. The ball head 20 is thus optimally fitted in the patient 4 in the direction of the viewing direction 14*a*, thus the frontal view in window 8*a*.

Figure 3:
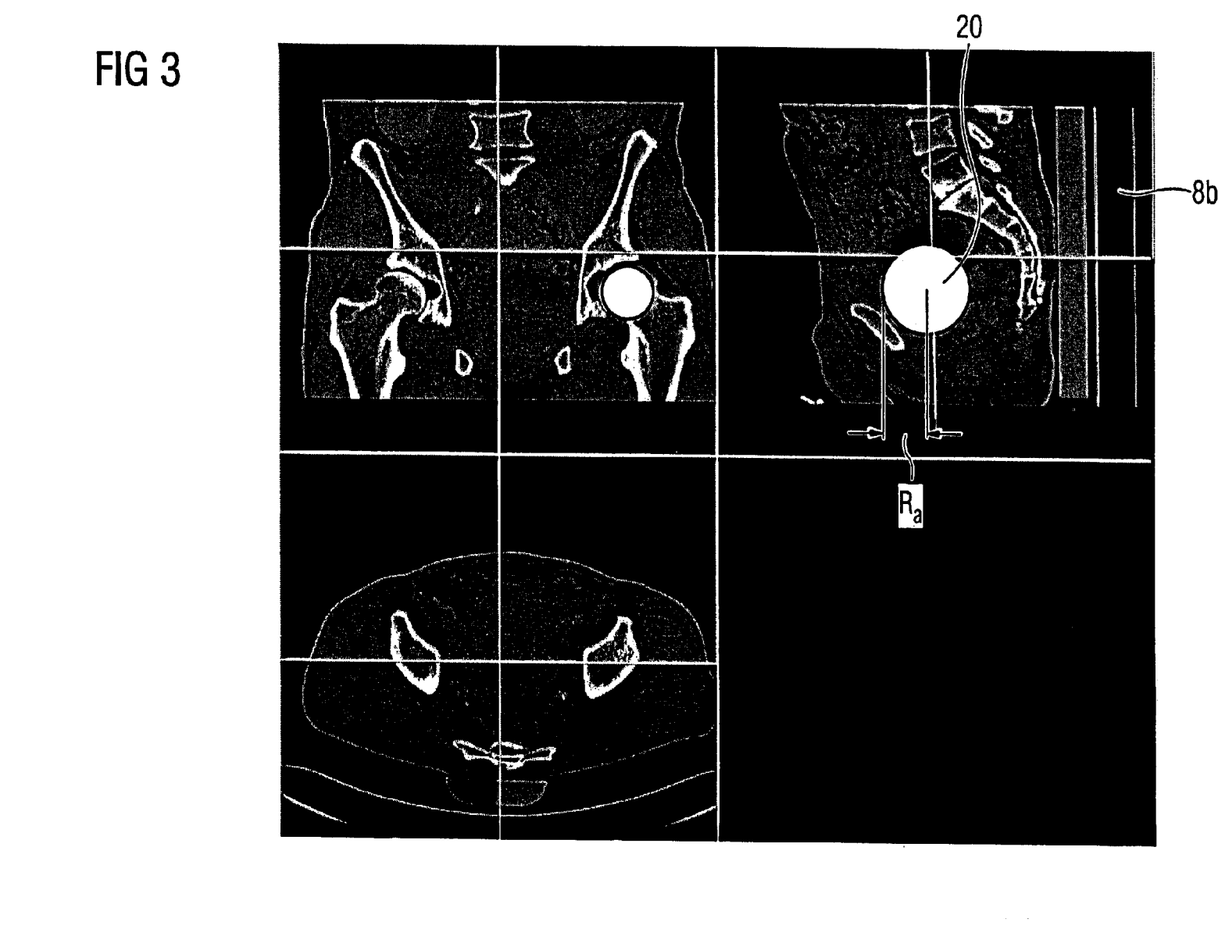
FIG. 3 shows the monitor of FIG. 2 with frontally fitted ball head of the hip prosthesis for additional lateral fitting.
Figure 4:
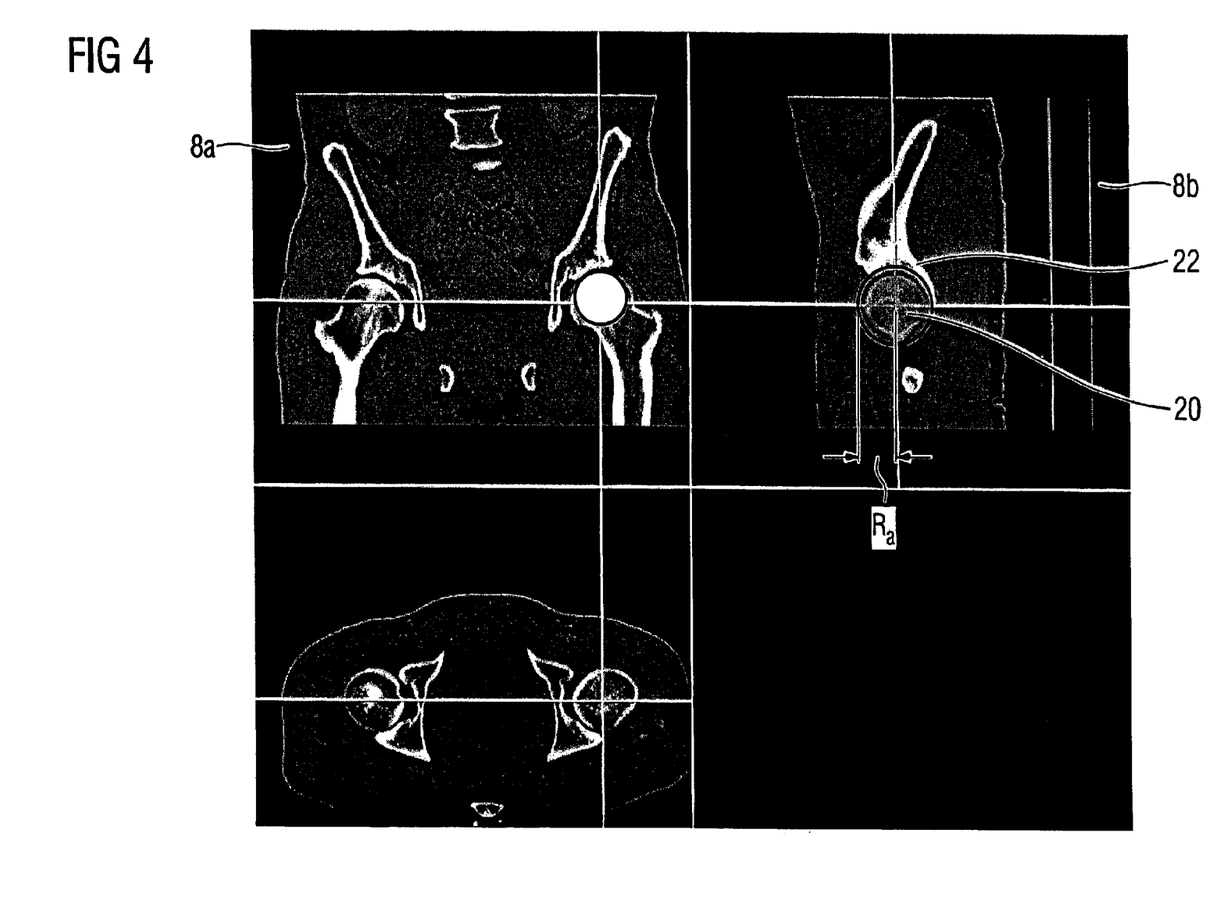
FIG. 4 shows the monitor of FIG. 3 with ball head laterally fit according to depth.
Figure 5:
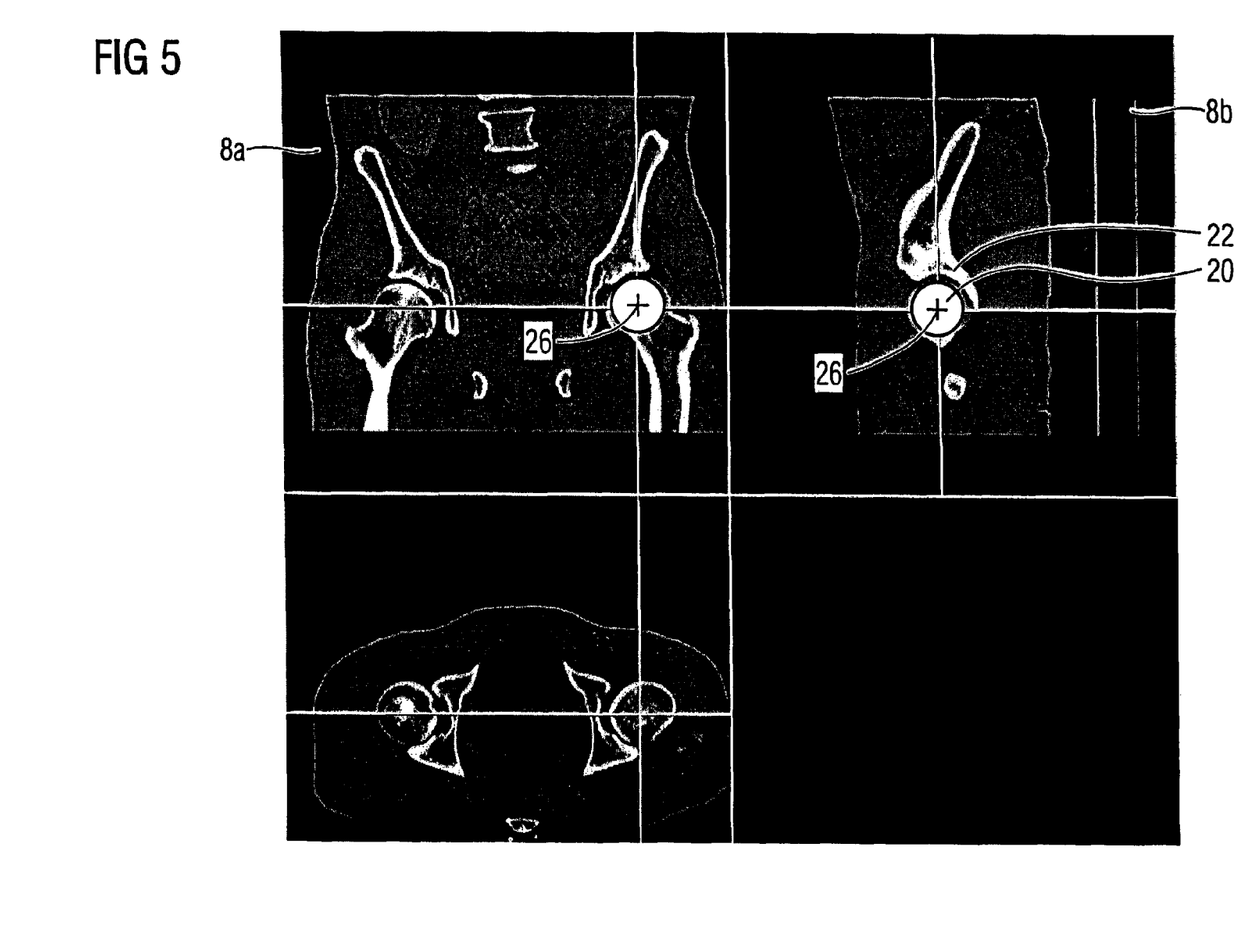
FIG. 5 shows the monitor of FIG. 4 with ball head laterally fit according to size.

The lateral view of the ball head 20 in the window 8*b* is now also shown in FIG. 3. This serves for the adaptation with regard to the lateral view in the window 8*b*. As described for the frontal adaptation, the lateral adaptation is begun with a distinctly larger outer radius $R_a \gg R_i$ of the ball head 20. Starting from the start position in FIG. 3 in window 8*b*, the image data 18 are now displaced (selection of the slice depth) until an optimal adaptation of the ball head 20 relative to the acetabulum 22 and an optimal bearing of the rotation center 26 is achieved, which is shown in FIG. 4. In order to hereby not occlude the view of the acetabulum 22, the ball head 20 is shown partially transparent or with an outline. Starting from FIG. 4, the outer radius $R_a$ of the ball head 20 is then again reduced in size until an optimal installation in the acetabulum 22 is ensured. FIG. 5 shows the corresponding result after the automatic radius adaptation.

The already-determined frontal position of the rotation center 26 in window 8*a* is hereby always retained. According to FIG. 5, the bearing of the rotation center 26 has now been determined and it is then enabled for the physician 10 to effect an arbitrary rotation of the entire volume image in all windows 8*a*-8*c*, thus of the image data 16 and 18 that are permanently linked relative to one another, thus of the patient 4 with fixed ball head 20. The physician can hereby check whether the later hip joint 2 can rotate perfectly without receiving disruptive contact in the previous natural joint socket 22. Manual corrections with regard to position and radius are still possible.

Figure 6:
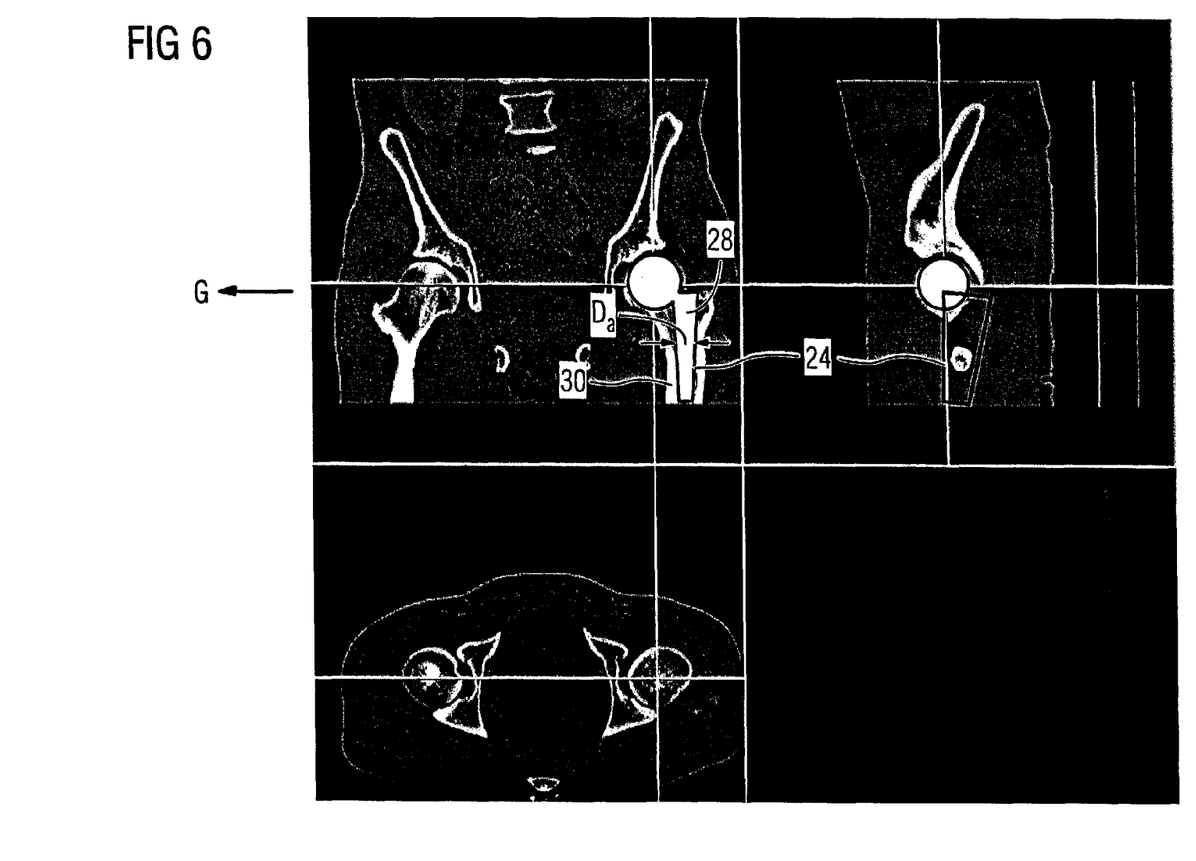
FIG. 6 shows the monitor of FIG. 5 with frontally fit shaft of the hip prosthesis.

Derived from the position of the rotation center 26 of the ball head 20 (established according to FIG. 5) in connection with data from the aforementioned representative set (patient collective), the approximate bearing and orientation of the implant shaft 24 relative to the image data 18 or the patient 4 are known corresponding to the bearing of the ball head in FIG. 2. FIG. 6 shows the corresponding shaft 24 blended (faded) into the monitor image from FIG. 5. As a next step, the inner contour 28 of the femur 30 of the patient 4 is calculated from the image data 18 after a well-established segmentation method. The shaft contour (provided, for example, from the database 12) of the shaft 24 of the currently selected hip joint 2 is likewise enlarged in window 8*a* corresponding to the ball head 20 in FIG. 3, such that said shaft contour in every case has a larger outer diameter $D_a$ than the inner diameter $D_i$ of the femur 30. An initial measure G of the congruence, thus the quality of the adaptation of the shaft 24 in femur 30, is calculated via the cross-correlation (or another measure) of the enlarged implant contour ($D_a$) of the shaft 24 with the inner contour 18 of the femur ($D_i$). As explained above with regard to the ball head 20, the depth in the 3D image data 18 (thus the corresponding slice depth in window 8*a*) is iteratively altered such that the adaptation of shaft 24 and femur 30 is improved and a maximum is finally reached. The value G calculated from the aforementioned correlation is used for this, for example. From this point in time of the adaptation, the original, true-to-scale implant contour (thus the corresponding dimensions of the shaft 24) is used.

The rotation of the shaft 24 in the image plane around an axis 32 directed away from the viewer (see FIG. 1) subsequently ensues iteratively. The iterative rotation around the horizontal axis 34 (see FIG. 1) follows this until here as well an optimum of the adaptation is achieved. As can be seen in image 14*a*, the rotation around axis 34 can also be controlled via a rotation in the image plane in image 14*b*, and the horizontal axis 34 in image 14*a* correspondingly emerges as an axis parallel to the optical axis in image 14*b*, assuming orthographic projection.

Figure 7:
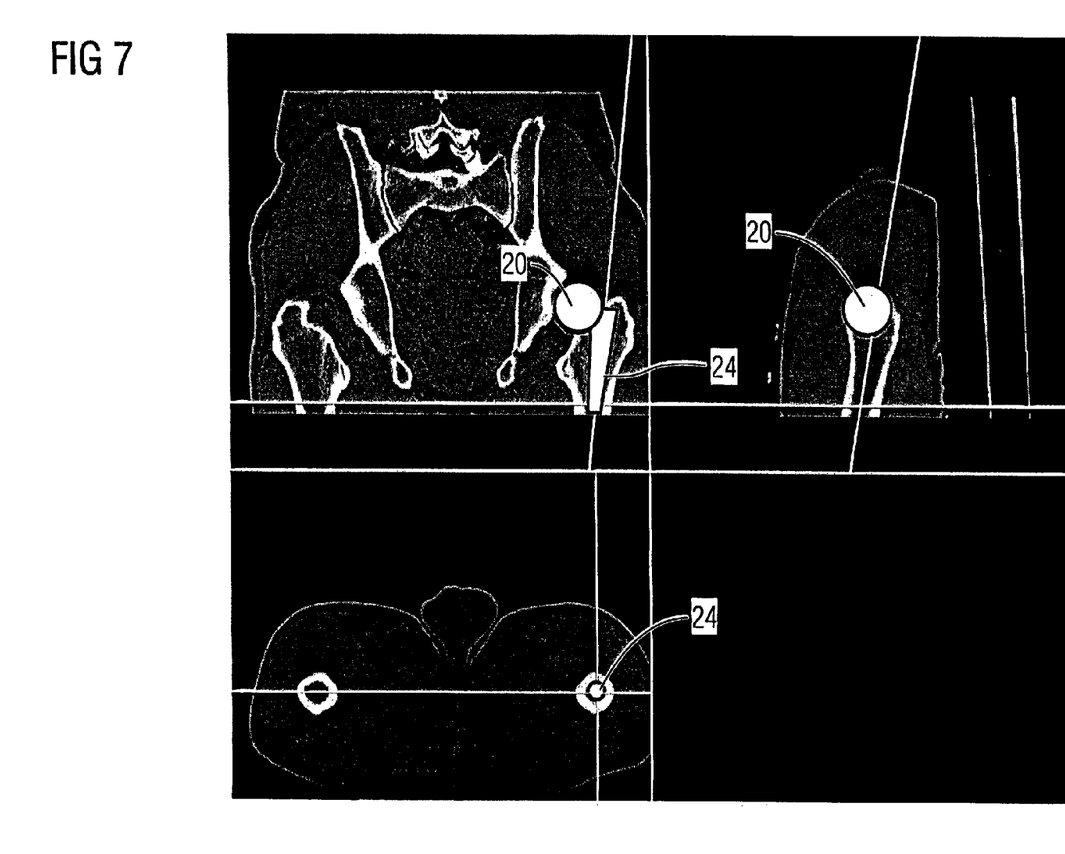
FIG. 7 shows the monitor of FIG. 6 with frontally fit and axially fit shaft.

Alternatively (as described above for the ball head 20), here an optimized implant diameter can be determined, possibly with reference to the corresponding position and orientation relative to the femur 30. Further paired depth variations of the slice depths in the windows 8*a*-8*c* and rotations are implemented with the updated size (and therewith contour) of the shaft 24 until the adaptation can no longer be further improved. The optimal position (maximum shaft width in the femur 30) has thus been found for the hip joint 2, which is shown in FIG. 7.

Figure 8:
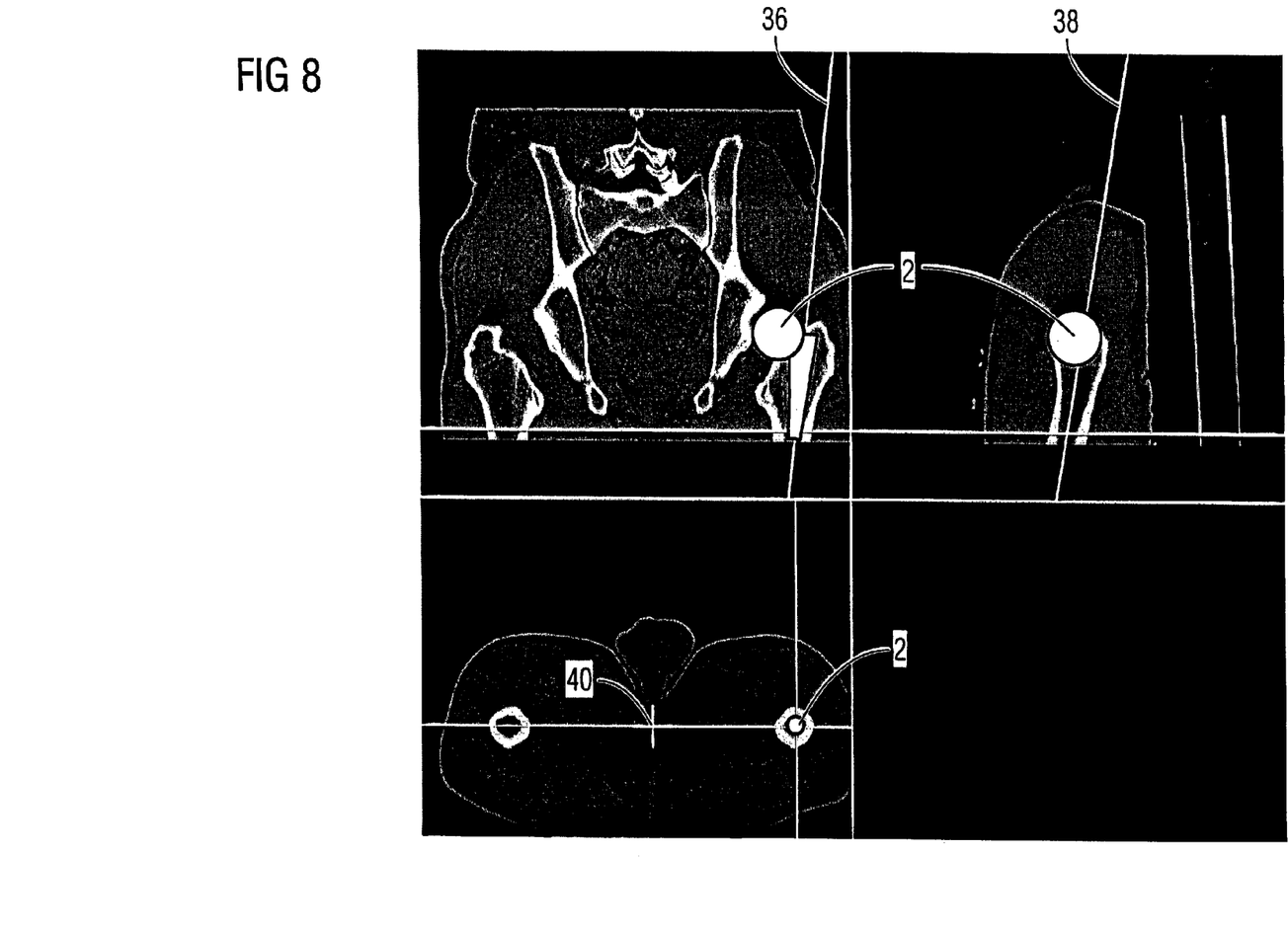
FIG. 8 shows the monitor of FIG. 7 completely fit hip prosthesis.

FIG. 8 shows the hip joint 2 situated in the optimal end position.

As noted above with regard to the ball head 20, the view of the image data 16 and 18 (which are fixed relative to one another) can now be monitored or, respectively, re-corrected via corresponding displacement and rotation.

For this the section lines 36, 38 in the windows 8*a*,*b* can be tilted or displaced in order to change the corresponding views of the respective other windows 8*b*, 8*a*. The representation in the window 8*c* can be rotated around the rotation center 40.

Alternatively, it is possible to rotate the implant shaft 24 alone into a new and fixed position relative to the windows 8*a*-*c*, whereby the image data 18 of the patient 4 are initially rotated as well. The newly fixed shaft 24 can then be fixed again and the image data 18 can again be displaced and rotated relative to this.

After determination of the correct positions of ball head 20 and shaft 24 of the hip joint 2, the prosthesis neck (not shown) connecting these two parts is automatically determined with the correct angulation and correct length and the hip joint 2 is thus completed virtually. The fit precision and the functionality of the hip joint 2 can subsequently be checked via new rotation and displacement of the complete hip joint 2 and primarily of the volume image, thus of the image data 18 of the patient 4. Experiences and knowledge of the biomechanics associated with the optimal orientation and position of the implant (thus of the hip joint 2) in the patient 4 can also be used.

For the aforementioned optimization of the adaptation (which ultimately is based on a correlation measure (cross-correlation coefficient) G), after a segmentation of, for example, acetabulum 22 or inner contour 28 in the patient 4 or of the patient's image data 18, said patient's geometric position is predominantly used. This is also the method of choice given SSD since SSD builds on a corresponding segmentation. In the shown MPR, or alternative VR and MIP representations, in which the implant models are three-dimensionally "filled in" from the databank 12 and their voxels are correlated with the respective range of voxels in the 3D volume data set (image data 18), the segmentation can be foregone.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for virtual adaptation of an object to be medically inserted into a patient, to a body part of the patient, comprising the steps of:
   obtaining contiguous 3D datasets of the object and the body part;
   based on the 3D datasets, displaying the object in a desired view on a monitor screen;

based on the 3D datasets, also displaying the body part on the monitor screen;

automatically displacing the body part, in an unchanged 3D volume imaging context, relative to the object on the monitor until the object is adapted to the body part on the monitor screen, while maintaining a position and an orientation of the object relative to the monitor screen unchanged, and modifying a depth position of the 3D dataset at least once relative to the monitor screen;

allowing automatic or manual modification of dimensions of the object on the monitor screen to produce an altered object on the monitor screen; and automatically again adapting the altered object to the body part on the monitor screen by enlarging or decreasing said dimensions of the object on the monitor screen in order to alter said dimensions to scale with regard to the body part on the monitor screen.

2. A method as claimed in claim 1 wherein said object is an implant, and comprising modifying the dimensions of implant by selecting an implant from an implant data bank.

3. A method as claimed in claim 1 wherein said object is an implant comprising two implant components, and automatically or manually altering respective ones of said two implant components by selecting respective ones of said two implant components from a component data bank.

4. A method as claimed in claim 1 wherein 2D data representing the object are accessible by said monitor, and automatically generating 3D data representing said object from said 2D data, using known symmetries and prior knowledge of said object.

5. A method as claimed in claim 1 comprising displaying a three-dimensional representation of said object on said monitor.

6. A method as claimed in claim 1 comprising automatically displacing said object until the object is adapted to the body part by achieving a predetermined fit size.

7. A method as claimed in claim 1 comprising executing steps of a medical procedure on the patient dependent on a result of the adaptation of the object to the body part.

8. A method as claimed in claim 7 comprising implementing a procedure selected from the group consisting of inventory planning, material provisioning, and accounting, associated with said medical procedure, dependent on the adaptation of the object to the body part.

9. A method as claimed in claim 1 comprising, after adapting said object to said body part of the patient relatively fixing a portion of the 3D dataset representing the object and a portion of the 3D dataset representing the body part with respect to each other, to produce common movement and rotation of the object and the body part on the monitor screen.

* * * * *